United States Patent [19]
Hopkins et al.

[11] Patent Number: 5,712,229
[45] Date of Patent: Jan. 27, 1998

[54] WATERBORNE LUBRICANT FOR TEFLON PRODUCTS

[75] Inventors: David P. Hopkins, Salt Lake City; Mohammad A. Khan, Sandy, both of Utah

[73] Assignee: Becton Dickinson and Company, Franklin Lakes, N.J.

[21] Appl. No.: 762,360

[22] Filed: Dec. 9, 1996

Related U.S. Application Data

[63] Continuation-in-part of Ser. No. 568,886, Dec. 7, 1995, abandoned.

[51] Int. Cl.⁶ .................................. C10M 107/50
[52] U.S. Cl. ........................................... 508/202
[58] Field of Search ................................ 508/202

[56] References Cited

U.S. PATENT DOCUMENTS

| | | | |
|---|---|---|---|
| 3,574,673 | 4/1971 | Schweiger et al. | 117/132 |
| 3,912,665 | 10/1975 | Spitzer et al. | 260/2.5 E |
| 4,269,739 | 5/1981 | Grejsner | 508/211 |
| 4,588,398 | 5/1986 | Daugherty et al. | 604/265 |
| 4,661,300 | 4/1987 | Daugherty | 264/40.6 |
| 4,664,657 | 5/1987 | Williamitis et al. | 604/265 |
| 4,758,595 | 7/1988 | Ogunbiyi et al. | 514/635 |
| 4,814,231 | 3/1989 | Onohara et al. | 428/425.5 |
| 4,836,986 | 6/1989 | Ogunbiyi et al. | 422/28 |
| 4,837,047 | 6/1989 | Sato et al. | 422/41 |
| 4,838,876 | 6/1989 | Wong et al. | 604/265 |
| 4,842,889 | 6/1989 | Hu et al. | 427/38 |
| 4,844,986 | 7/1989 | Karakelle et al. | 428/447 |
| 4,904,433 | 2/1990 | Williamitis | 264/130 |
| 4,973,643 | 11/1990 | O'Lenick, Jr. | 528/15 |
| 5,013,717 | 5/1991 | Solomon et al. | 514/56 |
| 5,026,607 | 6/1991 | Kiezulas | 428/423 |
| 5,037,419 | 8/1991 | Valentine et al. | 604/408 |
| 5,047,159 | 9/1991 | Zehler | 252/49.6 |
| 5,061,738 | 10/1991 | Solomon et al. | 523/100 |
| 5,071,706 | 12/1991 | Soper | 428/402.2 |
| 5,185,006 | 2/1993 | Williamitis et al. | 604/265 |
| 5,266,359 | 11/1993 | Spielvogel | 427/388.4 |
| 5,272,012 | 12/1993 | Opolski | 428/423.1 |
| 5,336,209 | 8/1994 | Porzilli | 604/307 |
| 5,338,312 | 8/1994 | Montgomery | 604/230 |
| 5,344,411 | 9/1994 | Domb et al. | 604/265 |
| 5,383,903 | 1/1995 | Totakura | 606/228 |
| 5,409,463 | 4/1995 | Thomas et al. | 604/167 |
| 5,431,832 | 7/1995 | Crowe et al. | 508/211 |
| 5,549,836 | 8/1996 | Moses | 508/211 |

FOREIGN PATENT DOCUMENTS

| | | |
|---|---|---|
| 0 627 474 A1 | 12/1994 | European Pat. Off. . |
| 0 698 463 A2 | 2/1996 | European Pat. Off. . |
| 0 709 103 A1 | 5/1996 | European Pat. Off. . |

OTHER PUBLICATIONS

Union Carbide Chemicals and Plastic Company, Inc., Material Safety Data Sheet for Y-12686, Effective Date Jun. 1, 1992, Danbury, CT.

Union Carbide Chemicals and Plastic Company, Inc., Material Safety Data sheet for Y-12613, Effective Date Sep. 17, 1992, Danbury, CT.

Hoffman-LaRoche, Inc., Material Safety Data Sheet for d,1-alpha-Tocopheral, Effective Jul. 20, 1992, Nutley, NJ.

W. Nikolowski, Vitamin E. in Dermatology, VITAMINS, pp. 1–6, 1973.

ICI Americas Inc., Cosmocil CQ Brochure.

ICI Americas Inc.; Baquacil Brochure.

Union Carbide Chemicals and Plastics Company Inc., Silwet Surfactants Brochure.

The United States Pharmacopeia, pp. 1451–1453, 1990, Rockville, MD.

*Primary Examiner*—Jacqueline V. Howard
*Attorney, Agent, or Firm*—Eric M. Lee

[57] ABSTRACT

This invention relates to a new water soluble lubricant for a medical device, such as a catheter and an introducer needle. The lubricant is a silicone surfactant which is non-ionic and which is a good lubricating fluid. Preferably the silicone surfactant that is used is a block copolymer polyalkylene oxide-modified polydimethylsiloxane. Water is used as the solvent for this lubricant. The lubrication solution includes a solution stabilizer to clarify the solution and antimicrobial agents to inhibit microbial growth in the water solution or on the coated product. Vitamin E or its derivatives may also be used in the lubrication solution. When the lubrication solution is used to lubricate Teflon products, a small amount of a low molecular weight alcohol is added to the lubrication solution to increase wettability.

5 Claims, No Drawings

WATERBORNE LUBRICANT FOR TEFLON PRODUCTS

This application is a continuation-in-part of application Ser. No. 08/568,886, filed Dec. 7, 1995 now abandoned.

BACKGROUND OF THE INVENTION

This invention relates in general to a novel lubricant for medical devices, in particular intravenous (IV) catheters. IV catheters are generally used on patients to infuse liquids, such as normal saline, glucose solutions and drugs, into the patient. These catheters are also used to withdraw blood from the patient for blood gas and other analysis.

In order to place a catheter in a patient's vein, a sharp introducer needle must be used to puncture the skin, tissue and vein wall to provide a path for placement of the catheter in the vein. Typical IV catheters are "over-the-needle" catheters where the catheter is coaxially placed over the needle. The distal tip of the catheter is located adjacent to and proximal of the sharp distal tip of the needle. Preferably the tip of the catheter adheres slightly to the tip of the needle to ensure that both the catheter and needle travel together through the skin, tissue and vein wall and into the patient's vein. The adherence is achieved by making the inner diameter of the catheter tip slightly smaller than the outer diameter of the needle.

Placement of the catheter and needle into the patient causes sharp pain to the patient. In order to facilitate insertion of the catheter and needle into the vein and to minimize patient discomfort, the catheter and needle can both be lubricated. Most IV catheters and needles are lubricated with polydimethylsiloxane silicone fluid. However, some IV catheters and needles are not lubricated at all.

The polydimethylsiloxane silicone fluid may be applied to the surface of the catheter and needle by wiping the surfaces with the lubricant. Alternatively, the catheter and needle can be separately dipped into a lubrication solution of polydimethylsiloxane silicone fluid and a solvent. This is generally the preferred method of applying the lubricant because a consistent, controlled and uniform coating can be achieved. The polydimethylsiloxane silicone fluid must be dissolved in an organic solvent because the silicone oil in this compound is hydrophobic. Typically, the solution contains 2.5% silicone oil.

Until recently the preferred solvent has been freon because it is non-flammable and flashes off, i.e. evaporates, readily after the polydimethylsiloxane silicone fluid solution has been applied to the catheter and needle. Although freon has been preferred, it does suffer some drawbacks. For instance, the high evaporation rate of freon causes the polydimethylsiloxane silicone fluid to concentrate on the surface of the solution in which the catheter and needle are dipped. Because of this high evaporation rate, the solution is difficult to control. Moreover, this solution is expensive because of the large loss of freon during the coating process. In addition, freon is a chlorofluorocarbon (CFC) which is thought to react with and destroy the earth's protective ozone layer. Thus the manufacture and use of such CFC's will eventually cease in the near future. As a result, other solvents will have to be used in order for silicone fluid to be applied to medical devices, such as catheters and needles, for use as a lubricant. Other solvents include alcohol and hydrocarbons. However, alcohol and hydrocarbons are highly combustible. Therefore, it is too dangerous to use large amounts of these solvents in manufacturing.

SUMMARY OF THE INVENTION

It is therefore an object of this invention to provide a lubricant for a medical device, such as a catheter and an introducer needle assembly, that does not require the use of a CFC as a solvent.

It is another object of this invention to provide a lubricant for a medical device, such as a catheter and an introducer needle assembly, that does not require the use of large amounts of flammable material for a solvent.

It is yet another object of this invention to provide a lubrication solution for a medical device, such as a catheter and an introducer needle assembly, that is inexpensive and easy to control.

It is still another object of this invention to provide a lubrication solution for a medical device, such as a catheter and an introducer needle assembly, that is "environmentally friendly".

The lubricant of this invention is a silicone surfactant, which is a good lubricating fluid. In addition, the silicone surfactant is preferably non-ionic because it may have lower toxicity than the ionic form. Since silicone surfactants are water soluble, water may be used as the solvent to provide a lubrication solution for application of the lubricant on the medical device. If medical devices formed from polytetrafluoroethylene, i.e. Teflon, are to be lubricated, small amounts of alcohol may be used in conjunction with water as the solvent. Alcohol facilitates wetting of the Teflon surface and promotes a uniform coating of the lubricant on the Teflon surface once the alcohol and water evaporate.

The lubrication solution may also include vitamin E or its derivatives to prevent degradation of the lubrication solution and to enhance the lubricity of the lubricant. In addition, the lubrication solution in which the medical device to be lubricated is dipped may include a solution stabilizer to clarify the lubrication solution and antimicrobial agents to inhibit microbial growth in the lubrication solution or on the coated medical device.

The above and other objects and advantages of the invention will be apparent upon consideration of the following detailed description.

DETAILED DESCRIPTION OF THE INVENTION

Although this invention is discussed in terms of its application to IV catheters and introducer needles, it is to be understood that this invention could be used on other medical devices where a lubricious surface on the device is desirable.

A silicone surfactant is used as the lubricant since it is a good lubricating fluid. The use of a silicone surfactant as the lubricant for IV catheters and introducer needles also reduces the likelihood of poor flashback through the needle lumen. This is because a surfactant tends to draw blood through the needle and does not resist blood flow as most silicone fluids do. Furthermore, the surfactant has a higher affinity for the catheter and needle. As a result, the surfactant improves coating uniformity and is less likely to be pushed out from between the catheter tip and needle, thus controlling adhesion between the catheter tip and the needle. Another benefit of using a silicone surfactant is that it is water soluble and can thus be applied to the surface to be lubricated in a solution of the silicone surfactant and water. The use of a water soluble lubricant for medical devices reduces some of the problems associated with prior lubrication solutions. For example, such a water based lubrication solution is relatively inexpensive and is easier to control than freon or alcohol based lubrication solutions. In addition, water is an "environmentally friendly" compound. When a Teflon surface is to be coated with the lubricant of this invention, a small amount of alcohol should be added to the water for use as the solvent. The alcohol should have a molecular weight less than or equal to 150 and should have the formula ROH where R is any alkyl or a substituted alkyl hydrocarbon group. It is important to use alcohols having a low molecular weight because as the molecular weight increases, the solubility of the alcohol in water decreases. In fact, alcohols having a molecular weight greater than 150 may not dissolve in water and will not provide a lubrication solution that will work in accordance with this invention. Preferably, isopropyl alcohol is used. The addition of alcohol to the water facilitates wetting of the Teflon surface, which is hydrophobic, by the lubrication solution and thus produces a uniform coating of the lubricant on the Teflon surface once the solvent evaporates.

The alcohol should comprise more than about 0% and less than about 30% of the lubrication solution. Preferably the alcohol should comprise between about 5% to about 20% of the lubrication solution. When alcohol comprises below 5% of the lubrication solution, the Teflon surface is poorly wetted with the solution. When the amount of alcohol increases, wettability increases. However, when alcohol comprises over 20% of the lubrication solution, flammability problems significantly increase making the lubrication solution difficult to handle.

The silicone surfactant should comprise between about 0.25% to about 40.0%, preferably from about 2.0% to about 6.0%, of the solution. Preferably, the silicone surfactant that is used is a Silwet silicone surfactant. Silwet is the trade name of a class of silicone surfactants sold by OSI specialties, Inc. These surfactants and polyalkylene oxide-modified polydimethylsiloxane block copolymers. They are similar to standard silicone fluids except the polydimethylsiloxane backbone has polyalkylene oxide side chains similar to non-ionic surfactants like poly-(oxyethylene) poly-(oxypropylene) block copolymers known as pluronic polyols. The side chains are terminated with either hydroxy or low alkoxy end groups. One of these surfactants, Silwet L7001 has a molecular weight of 20,000 and a viscosity of 1700 centistokes. Its chemical formula is shown below:

is used for making IV catheters. The similarity in chemical structure between these side chains and the soft segment of polyether urethane promote the surfactant's affinity for the catheter surface.

Although surfactants can be irritating or toxic depending on exposure levels, the Silwet silicone surfactants are copolymers of two polymeric materials, silicone fluids and polyalkylene oxides, which are low in toxicity. In particular, Silwet L7001 has a very low order of acute toxicity by swallowing, or skin penetration and is minimally irritating to the skin and is not irritating to the eyes. Thus, there should be no toxicity problems when the lubricant of this invention is used on a patient.

EXAMPLE NO. 1

Initial studies were conducted by separately dipping 20 gauge catheters and introducer needles into 4%, 8% and 32% Silwet L7001 silicone surfactant and water solutions and then assembling the catheters and needles. The assemblies were penetration tested through 13.5 mil. thick natural latex film.

|  | 4% Silwet L7001 | 8% Silwet L7001 | 32% Silwet L7001 |
| --- | --- | --- | --- |
| Needle tip (g) | 24.5 (0.9) | 23.3 (2.9) | 24.3 (5.8) |
| Needle transition (g) | 18.5 (2.7) | 17.0 (2.2) | 15.0 (1.0) |
| Needle heel (g) | 11.0 (0.7) | 10.5 (1.5) | 8.0 (0.0) |
| Catheter tip (g) | 26.0 (3.7) | 28.3 (5.3) | 25.3 (1.9) |
| Catheter taper (g) | 15.3 (0.8) | 15.0 (3.0) | 10.3 (0.8) |
| Catheter drag (g) | 7.3 (1.9) | 4.5 (0.5) | 4.0 (0.0) |

NOTE: () = standard deviation. Sample size = 4.

The values given represent the resistance in grams when the device is penetrated through the latex membrane. These values are comparable to those of currently marketed products that are lubricated with dimethylsiloxane fluids and are better than products that are unlubricated. This example thus shows that a silicone surfactant works as a lubricant for a catheter and/or introducer needle.

The lubrication solution may also include vitamin E or its derivatives. Preferably 0.1% to about 1.0% of vitamin E or

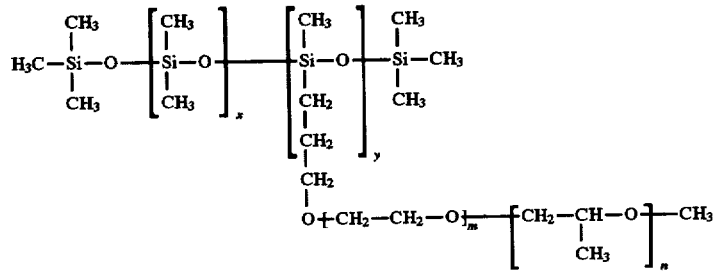

The amino-modified silicone polyether copolymer can also be used as the lubricant alone or in combination with the polyalkylene oxide-modified polydimethyl-siloxane block copolymer. These surfactants are soluble in a wide variety of solvents such as CFC, alcohol, acetone, and water. The polyalkylene oxide chains also promote wetting on polyether urethane surfaces. Polyether urethane is a material that its derivative is used. Vitamin E, which is known as alpha-tocopherol, is an antioxidant and thus prevents degradation of the solution. Vitamin E and its derivative vitamin E acetate are both oily products and enhance the lubricity of this lubrication system. In addition, vitamin E and its derivative prevent degradation of the lubrication solution. The molecular structure of vitamin E is given below:

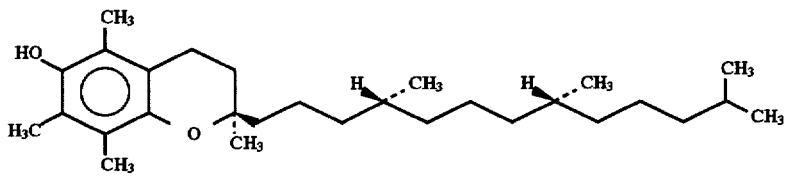

Since the lubrication solution is prepared in water, it is highly desirable that a small amount of an effective antimicrobial agent be present to serve as a preservative. In the absence of such an agent micro-organisms may grow in the silicon and make the solution toxic. There are several commercial antimicrobial agents available. These are iodophors; phenols; phenolic compounds such as para-chloro-meta-xylenol; biguanides such as chlorhexidine gluconate and polyhexamethylene biguanide hydrochloride (cosmocil). Cosmocil is used because it is less toxic than the other antimicrobial agents and is used as a preservative in contact lens cleaning solutions. The molecular structure of cosmocil is given below:

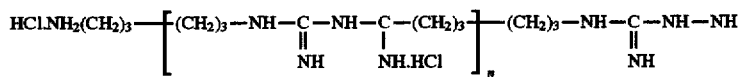

The molecular weight of this product is 2100±300. The antimicrobial agent should comprise between about 0.001% to about 5.0%, preferably between about 0.002% to about 0.05%, of the lubrication solution.

EXAMPLE NO. 2

20 gauge catheters and needles were separately dipped in a solution containing 8% Silwet L7001 silicone surfactant, 0.25% vitamin E, 0.5% vitamin E acetate, and 0.026% cosmocil. The catheters and needles were then assembled and these assemblies were penetration tested through 13.5 mil. thick natural latex film. The results are shown below:

| | |
|---|---|
| Needle tip (g) | 18.3 (1.9) |
| Needle transition (g) | 14.7 (0.6) |
| Needle heel (g) | 7.0 (0.3) |
| Catheter tip (g) | 20.2 (2.3) |
| Catheter taper (g) | 10.5 (0.6) |
| Catheter drag (g) | 3.5 (1.3) |

NOTE: () = standard deviation. Sample size = 5

It can be seen that the use of vitamin E and/or its derivatives in the solution improve the penetration forces.

When vitamin E and/or its derivatives are included in the lubrication solution, a rather cloudy solution is obtained indicating that the solution is not homogenous. If a quaternary ammonium salt is added at a certain concentration, a clear solution is obtained. For example, Sylguard, sold by Dow Corning, which is a reactive quat and benzalkonium chloride can be added to the solution. Other quaternary ammonium salts, such as benzethonium chloride, could also be used. The solution stabilizer should comprise between about 0.1% to about 10%, preferably between about 0.2% to about 1.0%, of the lubrication solution.

EXAMPLE NO. 3

A solution containing 6.0% Silwet L7001 silicone surfactant, 0.36% vitamin E and 1.0% benzalkonium chloride was used as the lubrication solution. In this example, the 1.0% benzalkonium chloride was in the form of 2.0% Hyamine 3500. Hyamine 3500 is a trade name for the benzalkonium chloride solution sold by Rohm and Hass and contains 50% of the active ingredient. As a comparison, a lubrication solution with no benzalkonium chloride was also used. 18 gauge catheters and needles were separately dipped and then assembled. These catheter assemblies were penetrated through dental dam (natural latex film).

| | No Quaternary Ammonium Salt | 1% Benzalkonium Chloride |
|---|---|---|
| Needle tip (g) | 24.3 (4.6) | 24.0 (3.6) |
| Needle transition (g) | 19.0 (1.0) | 19.3 (1.4) |
| Needle heel (g) | 11.3 (1.2) | 10.0 (0.5) |
| Catheter tip (g) | 19.8 (2.1) | 24.2 (2.3) |
| Catheter taper (g) | 15.5 (0.9) | 17.3 (1.8) |
| Catheter drag(g) | 4.8 (0.5) | 4.9 (0.4) |

NOTE: () = standard deviation.

These results indicate that there is no adverse effect on the lubricant caused by using a quaternary ammonium salt in the lubrication solution.

EXAMPLE NO. 4

Since amino-modified silicones are lubricous when applied to metal surfaces, the following lubrication solutions were prepared.

| | Lubricant I | Lubricant II |
|---|---|---|
| Silicone Surfactant | 4.50 | 4.50 |
| Amino-modified silicone polyether copolymer | 0.00 | 0.50 |
| Vitamin E (%) | 0.25 | 0.25 |
| Cosmocil (PPM) | 50 | 50 |
| Water Q.S. to | 100 | 100 |

20 gauge catheter assemblies were assembled after dipping the catheters and the introducer needles separately into the above solutions. The tip adhesions force between the catheter and the needle was measured after aging the assemblies 90° C. for 2½ days. The results are tabulated below:

|  | Tip Adhesion (lbs) |
| --- | --- |
| Lubricant I | 0.348 (0.11) |
| Lubricant II | 0.188 (0.03) |

NOTE: () = standard deviation.

These test results indicate that the use of an amino-modified silicone-polyether copolymer does lubricate the metal surface better than the unmodified silicone surfactant alone.

EXAMPLE NO. 5

The following statistical experiment was run to optimize the formulation of the lubrication solution of this invention.

|  | Composition A | Composition B | Composition C |
| --- | --- | --- | --- |
| Catheter taper (g) | 320.0 (37.9) | 284.0 (34.0) | 327.9 (39.4) |
| Catheter drag (g) | 1.0 (8.0) | 46.0 (9.7) | 42.0 (11.2) |

NOTE: () = standard deviation. Sample size = 5.

These results on thick latex membrane show that the amount of silicone surfactant applied to the catheter and the needle has opposite effects on catheter drag and needle tip penetration. The higher the silicone surfactant concentration, the lower the drag, but at high lubricant concentrations the needle tip penetration value increases. On fresh cow skin, the needle tip penetration value decreased with increased concentration.

| Catheter Lubricant |  | Needle Lubricant |  |
| --- | --- | --- | --- |
| Silicone Surfactant | 4.75% ± 0.25% | Silicone Surfactant | 2.38% ± 0.25% |
| Amino-modified silicone polyether copolymer | 0.525% ± 0.025% | Amino-modified silicone polyether copolymer | 0.525% ± 0.025% |
| Vitamin E | 0.263% ± 0.013% | Vitamin E | 0.263% ± 0.013% |
| Cosmocil | 50 ppm | Cosmocil | 50 ppm |
| Water Q.S. to | 100 | Water Q.S. to | 100 |

The following table lists some of the composition variations used.

|  | Composition A | Composition B | Composition B |
| --- | --- | --- | --- |
| Silicone Surfactant | 3.0 | 4.5 | 6.0 |
| Amino-modified silicone polyether copolymer | 0.5 | 0.25 | 0.5 |
| Vitamin E (%) | 0.125 | 0.13 | 0.125 |
| Cosmocil (PPM) | 50 | 50 | 50 |
| Water Q.S. to | 100 | 100 | 100 |

20 gauge catheter assemblies were assembled after dipping the catheters and the introducer needles separately. After aging the assemblies at 90° C. for 2½ days, these assemblies were penetration tested through thick natural latex film of 86.7 mils. thickness. The thick latex was used because it is closer to the thickness of mammalian skin and because small differences in penetration forces are magnified. The results are tabulated below:

|  | Composition A | Composition B | Composition C |
| --- | --- | --- | --- |
| Needle tip (g) | 156.0 (11.7) | 150.4 (13.1) | 155.9 (9.5) |
| Catheter tip (g) | 90.6 (10.3) | 87.0 (10.5) | 98.3 (7.0) |
| Catheter drag (g) | 31.6 (2.9) | 32.0 (2.3) | 27.6 (1.8) |

NOTE: () = standard deviation. Sample size = 8.

The above assemblies were also aged at 90° C. for two weeks to simulate a five year shelf-life and penetration tested through fresh cow skin. The results are tabulated below:

|  | Composition A | Composition B | Composition C |
| --- | --- | --- | --- |
| Needle tip (g) | 237.0 (63.7) | 226.0 (68.6) | 209.0 (46.1) |
| Catheter tip (g) | 299.0 (53.5) | 379.0 (42.7) | 378.0 (41.2) |

20 gauge catheters and needles were assembled as before and penetration tested through natural latex film of 13.5 mils thickness. At the same time, commercial 20 gauge Insyte® catheter products were tested under the same conditions for comparison. The results are tabulated below:

|  | Experimental Sample | Commercial Sample |
| --- | --- | --- |
| Needle tip (g) | 22.6 (8.6) | 19.5 (5.7) |
| Needle transition (g) | 17.3 (1.9) | 13.4 (1.2) |
| Needle heel (g) | 10.9 (1.1) | 7.0 (0.6) |
| Catheter tip (g) | 18.1 (3.0) | 16.3 (2.4) |
| Catheter taper (g) | 16.2 (2.1) | 10.6 (1.0) |
| Catheter drag (g) | 4.8 (1.9) | 3.0 (0.6) |

NOTE: () = standard deviation. Sample size = 10.

As is evident, the results are comparable for the commercial product and the experimental sample. The commercial sample used polydimethylsiloxane silicone fluid as the lubricant.

EXAMPLE NO. 7

22 gauge catheters and needles were assembled as before using the formulations described in Example 6 and penetration tested through sheep skin on the hind legs just below the knee. The penetration forces were measured using sensitive force transducers. The data were collected on a computer for analysis. For comparison, commercial 22 gauge catheter and needle assemblies using polydimethylsiloxane silicon fluid as the lubricant were used. The results are summarized below:

|  | Experimental Sample | Commercial Sample |
| --- | --- | --- |
| Max. Catheter/Needle Tip (g) | 142.57 | 164.67 |
| Max. Catheter Drag (g) | 70.31 | 271.68 |

As is evident, the new lubricant is superior to the standard commercial product.

EXAMPLE 8

Polyurethane tubes were lubricated using the formulations of this invention described in Example 6 as well as polydimethylsiloxane silicone fluid. These tubes were implanted into the aorta of rabbits to determine the level of associated clotting and emboli formulations. After three days the animals were sacrificed and the tubes were examined while they were still in the aorta. Clotting, if present, was photographed and recorded to size, number and location. The kidneys were also examined for renal infarcts which would indicate that emboli had formed and traveled downstream to lodge in the small arteries of the kidney. The clotting resulting from the water based lubrication solution of the invention was less than the clotting resulting from the commercial lubricant. The calculated risk of clotting was three times less for the water based lubrication solution versus the commercial lubricant.

EXAMPLE 9

The following formulations were tested:

| Ingredients | Needle Lubricant | Catheter Lubricant "A" | Catheter Lubricant "B" |
|---|---|---|---|
| Silicone Surfactant | 2.38% ± 0.25% | 4.75% ± 0.25% | 4.75% ± 0.25% |
| Amino-modified silicone polyether copolymer | 0.525% ± 0.025% | 0.525% ± 0.025% | 0.525% ± 0.025% |
| Vitamin E | 0.263% ± 0.013% | 0.263% ± 0.013% | 0.263% ± 0.013% |
| Cosmocil | 50 ppm | 50 ppm | 50 ppm |
| Isopropyl Alcohol | — | — | 10.0 ± 0.5% |
| Water Q.S. to | 100 | 100 | 100 |

20 gauge Teflon catheters and needles were assembled by lubricating the needles first with the needle lubricant. The Teflon catheters were lubricated with either catheter lubrication solution "A" or catheter lubrication solution "B". The needles and Teflon catheters were put together making sure that the two groups of Teflon catheters were separated from each other. These assemblies were penetration tested through natural latex film of 13.5 mils thickness. At the same time, commercial 20 gauge Teflon catheter assemblies were tested under the same conditions for comparison. The results are tabulated below:

|  | Commercial Sample | Catheter Lubricant "A" Samples | Catheter Lubricant "B" Samples |
|---|---|---|---|
| Needle tip (g) | 15.2 (2.7) | 17.8 (4.5) | 15.5 (2.8) |
| Needle transition (g) | 12.6 (1.5) | 13.4 (1.2) | 14.1 (1.8) |
| Needle heel (g) | 5.7 (0.4) | 7.1 (0.8) | 7.8 (0.9) |
| Catheter tip (g) | 18.5 (2.8) | 22.2 (2.6) | 20.1 (2.1) |
| Catheter taper (g) | 10.8 (1.2) | 25.3 (5.1) | 15.1 (2.2) |
| Catheter drag (g) | 3.9 (0.6) | 14.0 (6.3) | 6.1 (2.0) |
| Sample Size | 20 | 10 | 20 |

NOTE: Parenthesis () = Standard Derivation

As can be seen, the results obtained with catheter lubrication solution "B" are comparable with commercial samples. This test indicated that the lubrication solution should, in addition to the rest of the ingredients, contain 10% isopropyl alcohol when a Teflon product is to be lubricated.

20 gauge Teflon catheters lubricated with catheter lubrication solution "B" were also penetrated through fresh cow skin. At the same time, commercial Teflon catheter assemblies were penetrated through cow skin under similar conditions. Test results are reported below:

|  | Commercial Sample | Catheter Lubricant "B" Samples |
|---|---|---|
| Needle tip (g) | 166.0 (37.9) | 146.0 (37.6) |
| Catheter tip (g) | 230.0 (35.9) | 220.0 (62.7) |
| Catheter taper (g) | 297.5 (45.5) | 304.0 (68.1) |
| Catheter drag (g) | 77.3 (11.3) | 60.3 (12.3) |
| Sample Size | 10 | 10 |

As can be seen, the overall performance of the test products was equal to or slightly better compared to the commercial product. These results indicate that approximately 10% isopropyl alcohol in the lubrication solution provides better lubrication to the surface of the Teflon catheter.

EXAMPLE 10

Surface tension of catheter lubrication solution "A" and catheter lubrication solution "B" was measured using a DuNouy Surface Tensiometer. The results are reported below:

| Lubricant | Surface Tension Dynes/Cm |
|---|---|
| Catheter Lubricant "A" | 34.3 |
| Catheter Lubricant "B" | 29.7 |

The above results further show that catheter lubrication solution "B", which has a lower surface tension, would provide better surface coating for Teflon products.

EXAMPLE 11

20 gauge Teflon catheter assemblies lubricated with catheter lubrication solution "A" and catheter lubrication solution "B" were examined under scanning electron microscope to check for surface morphology. The catheter surface lubricated with catheter lubrication solution "A" was not smooth and bigger droplets of lubricant were visible on the surface. The catheter surface lubricated with catheter lubrication solution "B" looked considerably smoother and the lubricant was well spread over the surface. Again, these results confirm that for Teflon products whose surface is difficult to lubricate, a catheter lubrication solution having a lower surface tension will more likely be able to provide homogenous coating compared to a lubrication solution having a higher surface tension value.

EXAMPLE 12

The following formulations were tested:

| | Catheter Lubrication Solution | | | | | | |
|---|---|---|---|---|---|---|---|
| Ingredients | I | II | III | IV | V | VI | VII |
| Silicone Surfactant | 4.75% | 4.75% | 4.75% | 4.75% | 4.75% | 4.75% | 4.75% |
| Amino-modified Silicone Polyether Copolymer | 0.525% | 0.525% | 0.525% | 0.525% | 0.525% | 0.525% | 0.525% |
| Vitamin E | 0.263% | 0.263% | 0.263% | 0.263% | 0.263% | 0.263% | 0.263% |
| Cosmocil | 50 ppm | 50 ppm | 50 ppm | 50 ppm | 50 ppm | 50 ppm | 50 ppm |
| Isopropyl Alcohol | 0% | 5% | 10% | 15% | 20% | 30% | 50% |
| Water Q.S. to | 100 | 100 | 100 | 100 | 100 | 100 | 100 |

The surface tension and flammability data of these formulations is provided below:

| Composition | Surface Tension (dynes/cm) | Flammability |
|---|---|---|
| I | 34.3 | No |
| II | 34.6 | No |
| III | 29.7 | No |
| IV | 29.3 | No |
| V | 28.0 | No |
| VI | 26.0 | Yes |
| VII | 24.7 | Yes |

As this data indicates, the surface tension of the various solutions improves when the isopropyl alcohol comprises a larger portion of the solution. However, once the isopropyl alcohol comprises 30% or more of the lubrication solution, it becomes flammable and thus difficult to handle.

Thus it is seen that a new lubricant is provided that does not require the use of a CFC or large amounts of flammable material for a solvent and a new lubrication solution is provided that is inexpensive and easy to control. In addition, the lubrication solution of this invention is safe, nontoxic and "environmentally friendly."

We claim:

1. A lubrication solution for a medical device, consisting essentially of:

about 2% to about 6% of a silicone surfactant lubricant;

less than about 30% of a low molecular weight alcohol; and the balance water.

2. The lubrication solution of claim 1, wherein the silicone surfactant lubricant is a block copolymer polyalkene oxide-modified polydimethylsiloxane.

3. The lubrication solution of claim 1, wherein the silicone surfactant lubricant is an amino-modified silicone polyether copolymer.

4. The lubrication solution of claim 2 wherein the silicone surfactant lubricant also includes an amino-modified silicone polyether copolymer.

5. The lubrication solution of claim 1 wherein the low molecular weight alcohol has a molecular weight less than or equal to 150.

* * * * *